(12) United States Patent
Voirin et al.

(10) Patent No.: US 6,312,961 B1
(45) Date of Patent: Nov. 6, 2001

(54) OPTICAL SENSOR USING AN IMMUNOLOGICAL REACTION AND A FLUORESCENT MARKER

(75) Inventors: Guy Voirin, Saint-Aubin; Rino Kunz, Steinmaur, both of (CH)

(73) Assignee: CSEM Centre Suisse D'Electronique et de Microtechnique SA, Neuchatel (CH)

( * ) Notice: Subject to any disclaimer, the term of this patent is extended or adjusted under 35 U.S.C. 154(b) by 0 days.

(21) Appl. No.: 09/317,273

(22) Filed: May 24, 1999

(30) Foreign Application Priority Data

May 22, 1998 (FR) .................................................. 98 06451

(51) Int. Cl.[7] .................................................. G01N 33/543
(52) U.S. Cl. ........................ 436/518; 356/317; 356/318; 356/319; 356/320; 385/4; 385/10; 385/12; 385/31; 385/37; 385/129; 385/130; 385/132; 422/82.05; 422/82.08; 422/82.11; 435/287.1; 435/287.2; 435/287.9; 435/288.7; 435/808; 436/164; 436/172; 436/524; 436/527; 436/805
(58) Field of Search ..................... 422/82.05, 82.08, 422/82.11; 435/287.1, 287.2, 287.9, 288.7, 808; 436/164, 172, 518, 524, 527, 805; 356/317, 318, 319, 320; 385/4, 10, 12, 31, 37, 129, 130, 132

(56) References Cited

U.S. PATENT DOCUMENTS

| | | | |
|---|---|---|---|
| 5,081,012 | * | 1/1992 | Flanagan et al. ...................... 435/7.9 |
| 5,082,629 | * | 1/1992 | Burgess, Jr. et al. ............. 422/82.11 |
| 5,631,170 | | 5/1997 | Attridge . |

FOREIGN PATENT DOCUMENTS

| | | |
|---|---|---|
| 89/09394 | * 10/1989 | (WO) . |
| WO9533198 | 12/1995 | (WO) . |
| WO9635940 | 11/1996 | (WO) . |

* cited by examiner

*Primary Examiner*—Christopher L. Chin

(57) ABSTRACT

A biosensor comprises a waveguide into which light is coupled by a diffraction grating. The sample to be analyzed is placed on a reaction region in which a component of the immunological reaction is provided, for example antibodies or antigens. Fluorescence is excited on the surface of the waveguide because of the presence of a marker for example, a labelled antigen or antibody. Fluorescence is decoupled from the waveguide by the coupling diffraction grating or another diffraction grating. The waveguide is made of a material emitting light when it is excited by the marker excitation beam. This latter emission has a peak wavelength different from that of the emission radiation due to the marker used in the immunological reaction. Waveguide material fluorescence emission provides a reference during measurement.

22 Claims, 6 Drawing Sheets

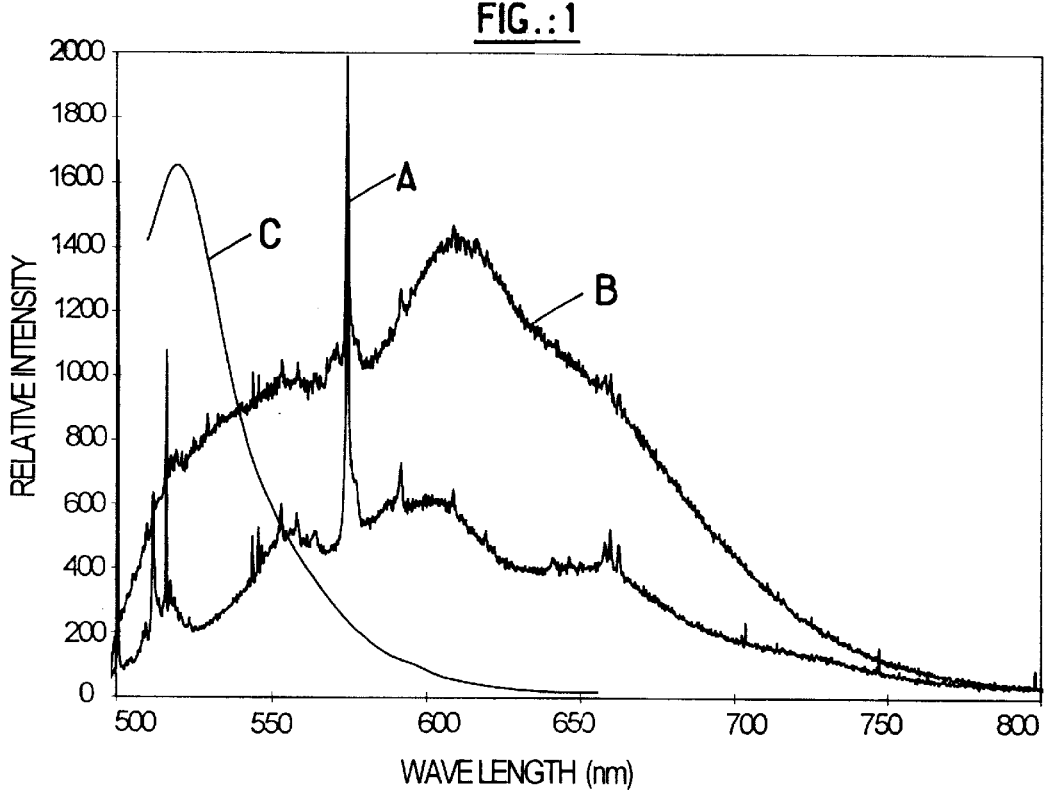
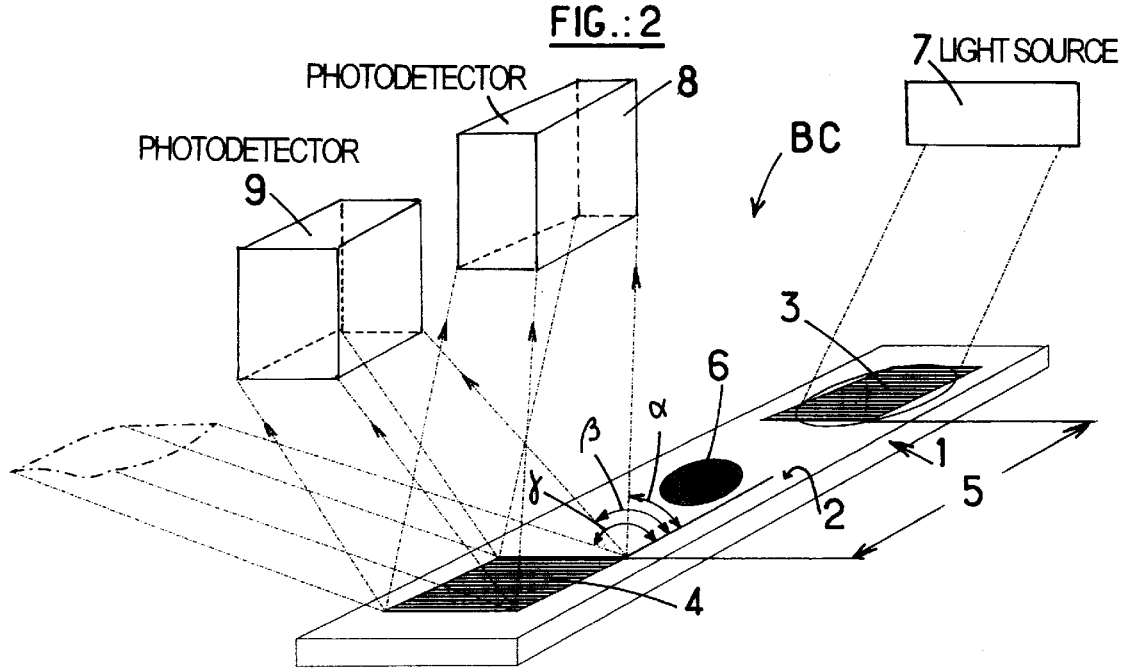

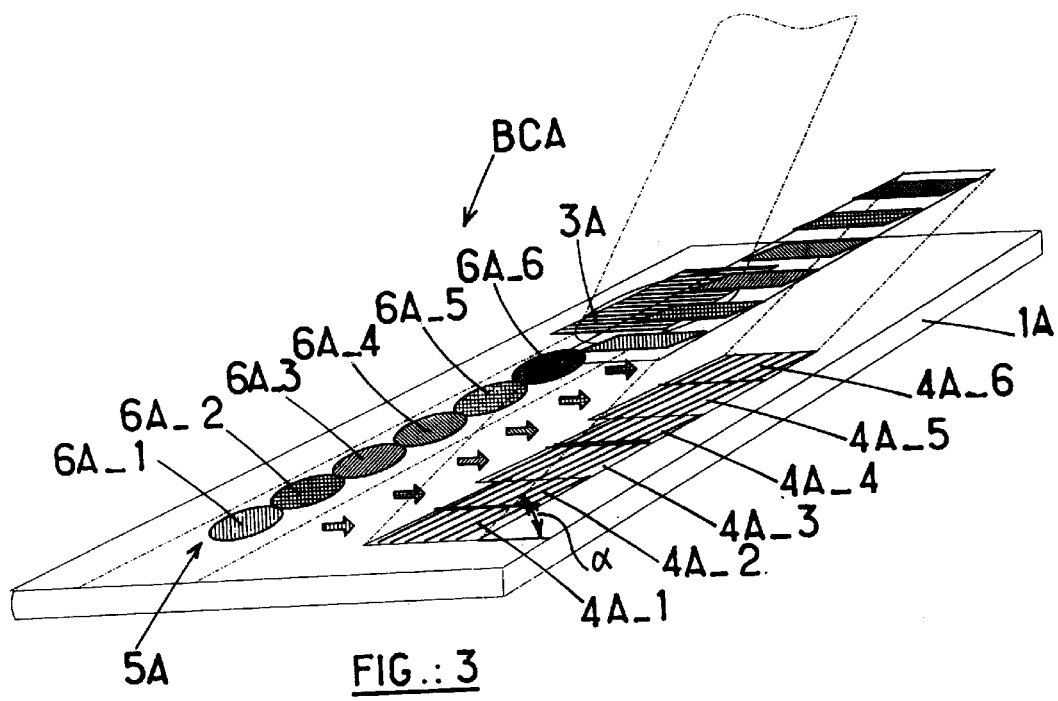
FIG.: 3
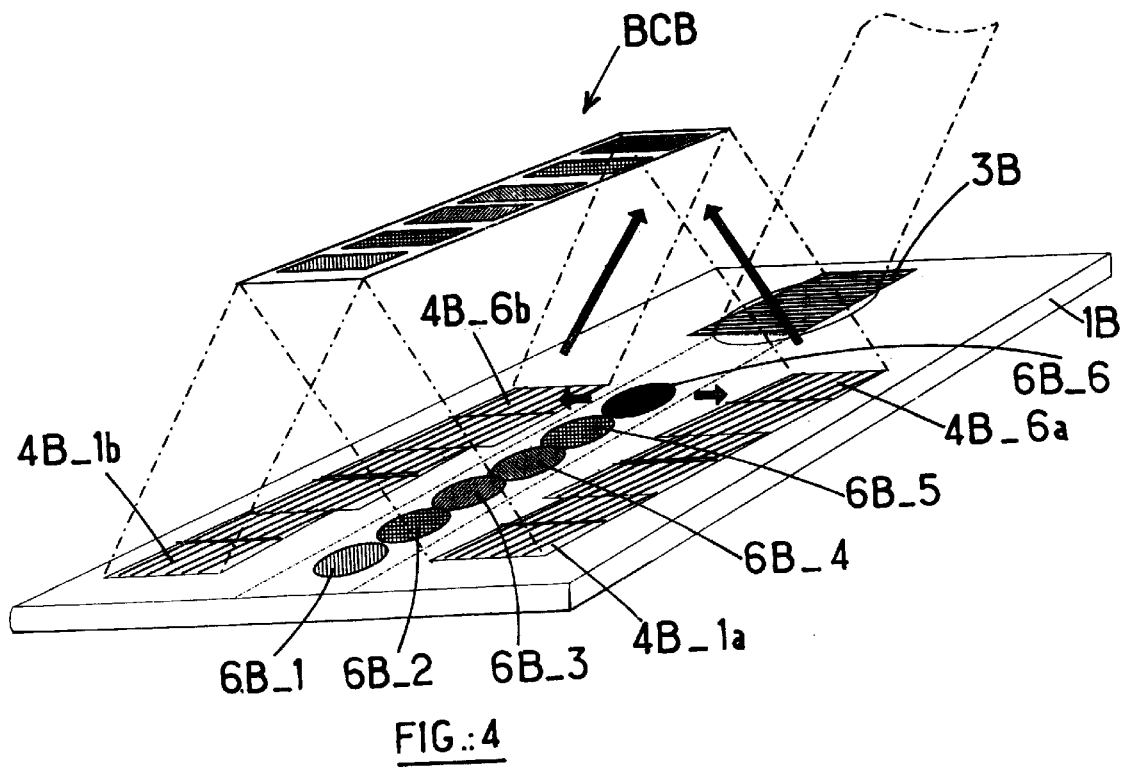
FIG.: 4

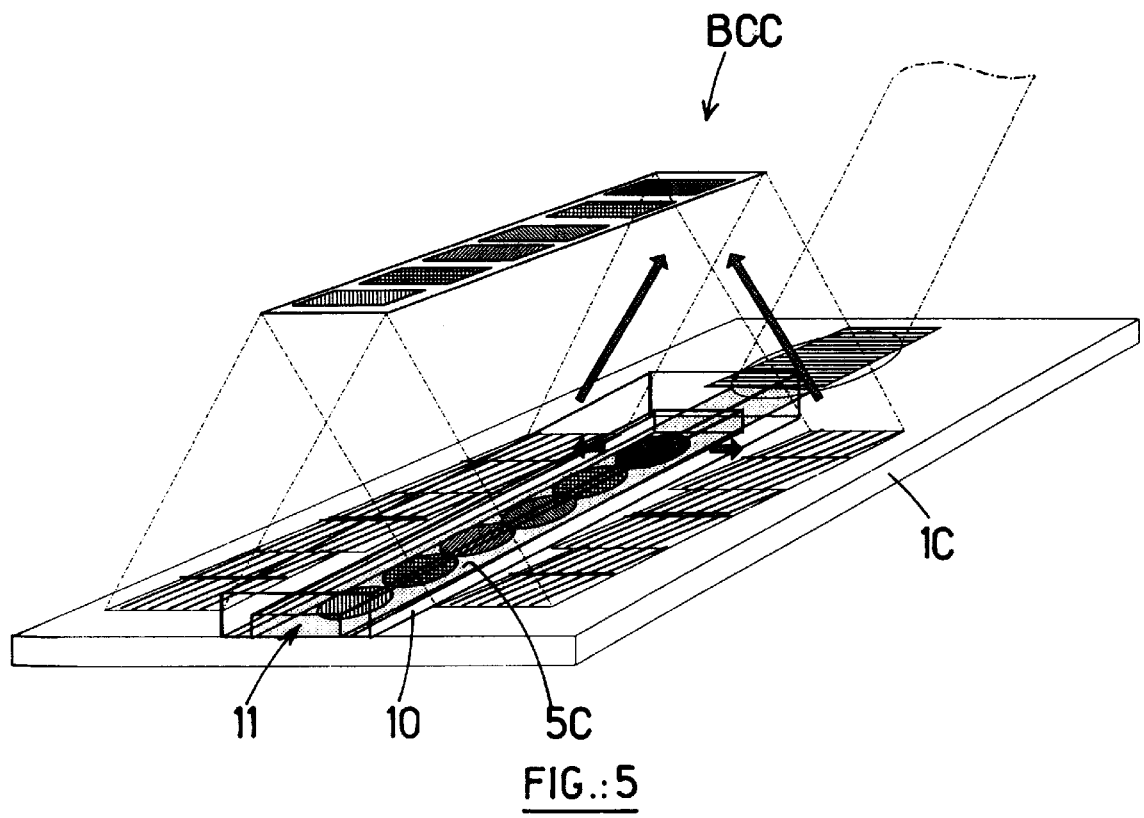
FIG.:5
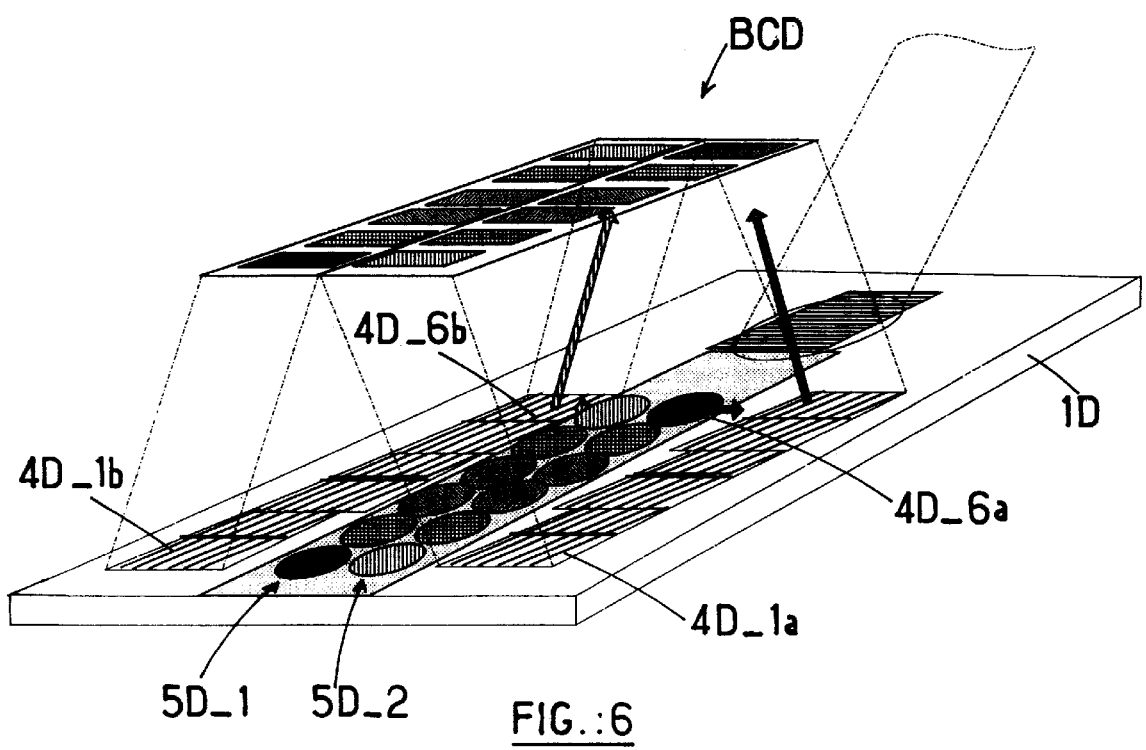
FIG.:6

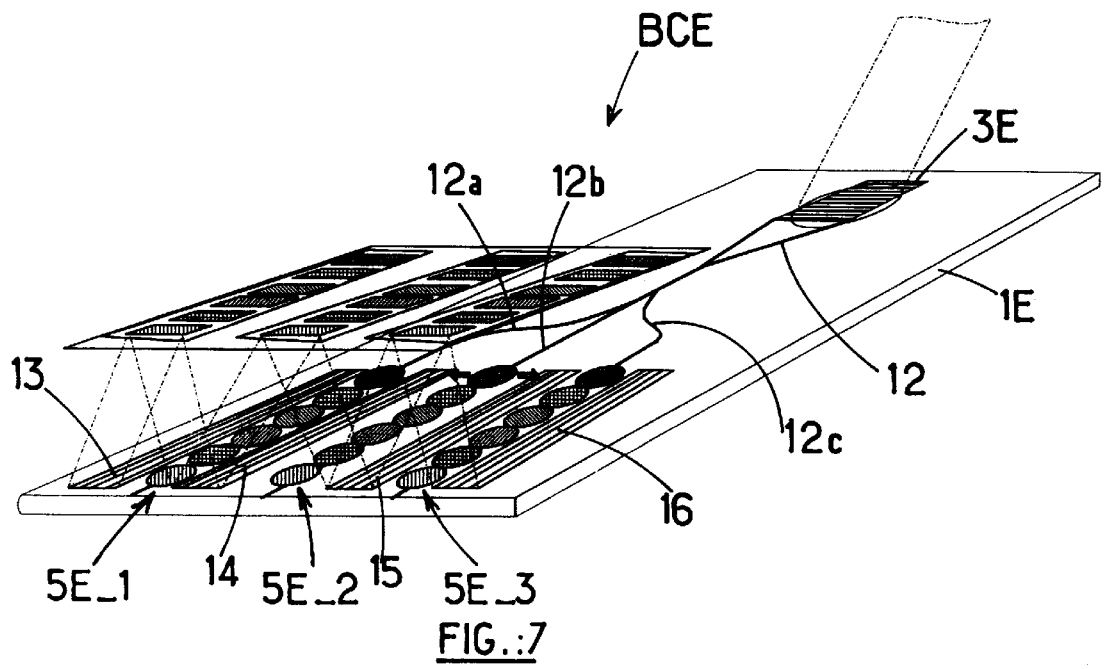
FIG.:7
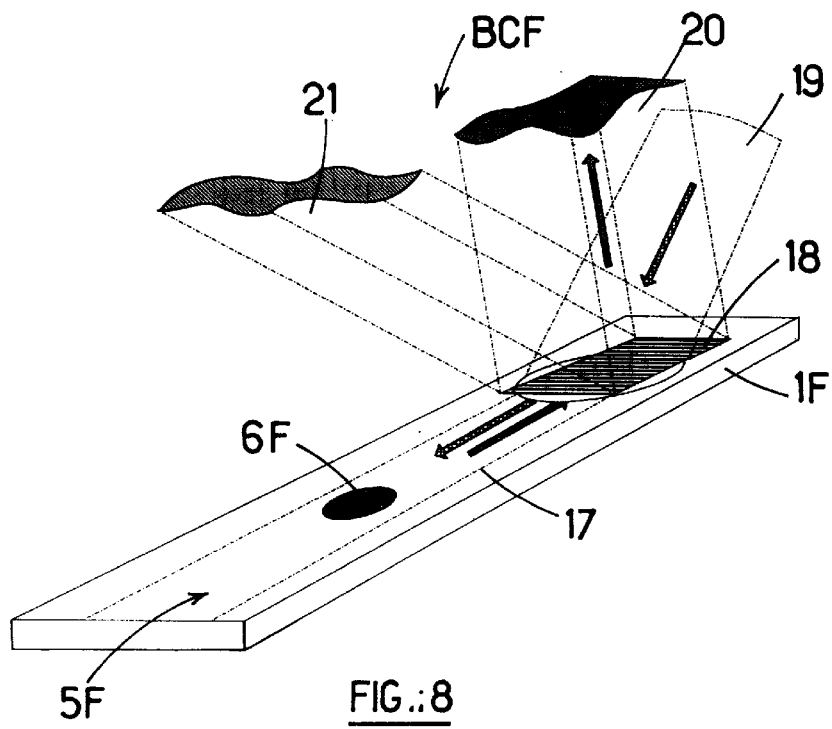
FIG.:8

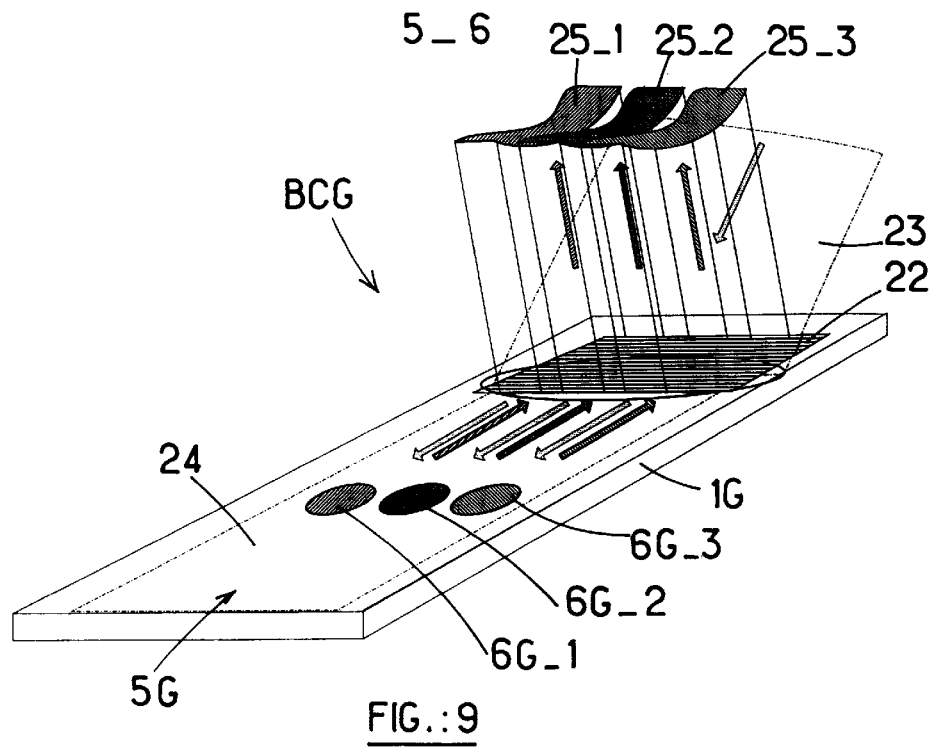
FIG.: 9
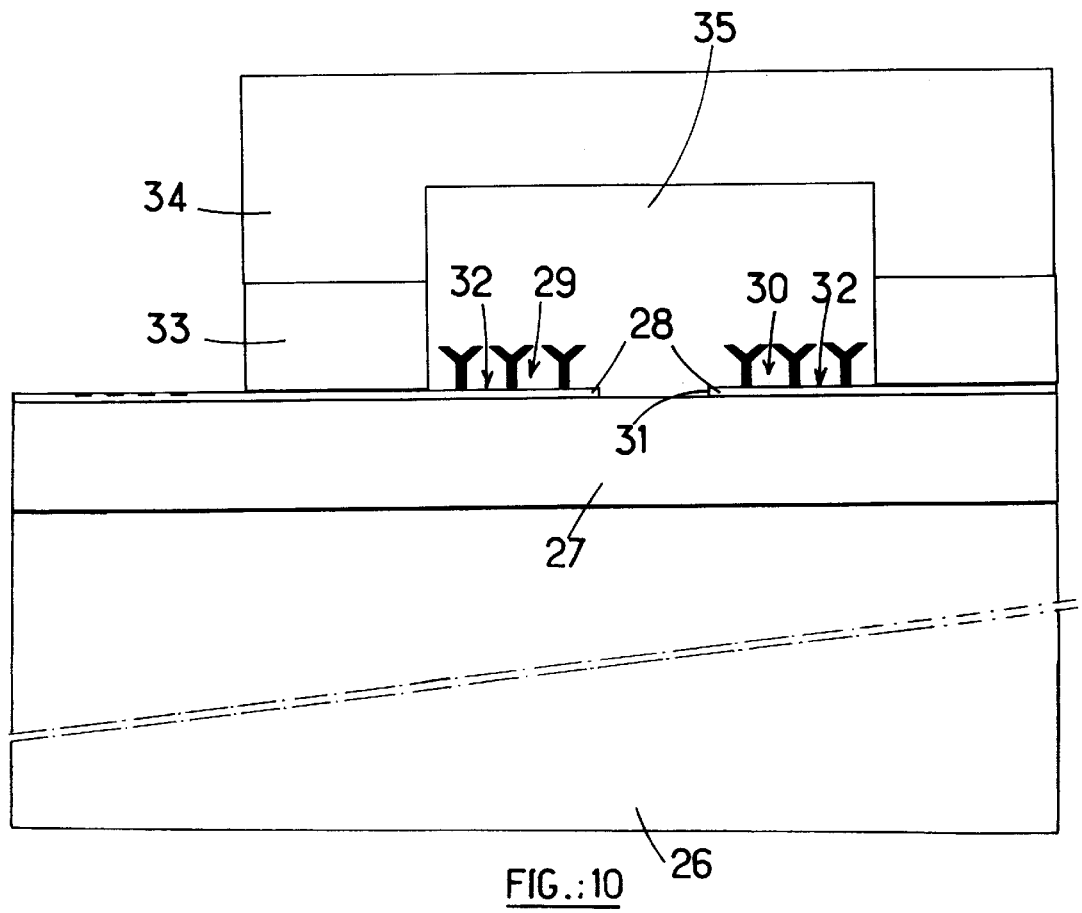
FIG.: 10

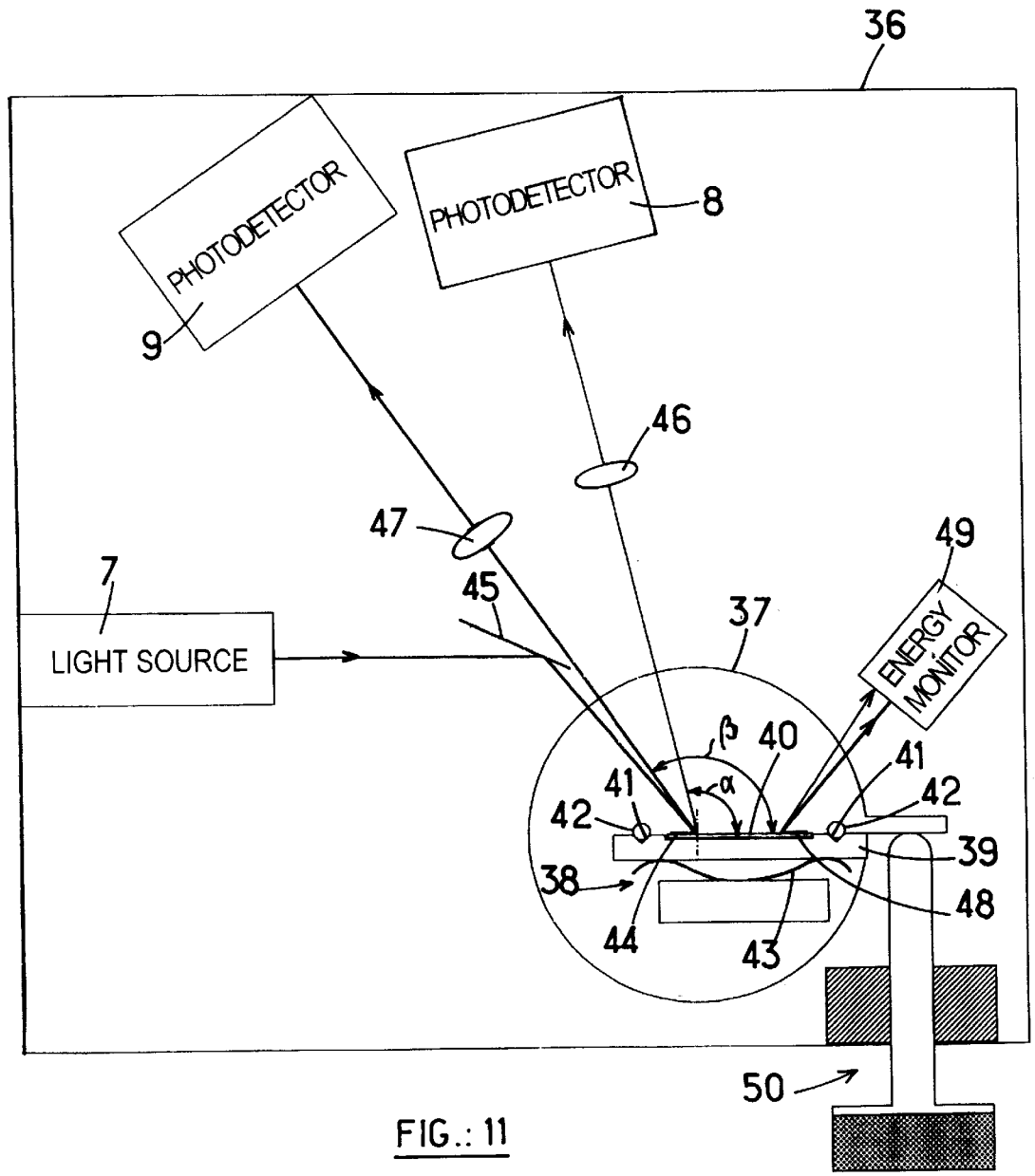
FIG.: 11

OPTICAL SENSOR USING AN IMMUNOLOGICAL REACTION AND A FLUORESCENT MARKER

BACKGROUND OF THE INVENTION

1. Field of the Invention

The present invention relates to an optical biosensor using an immunological reaction, a fluorescent marker and a detection principle based on measuring fluorescence and using an evanescent light wave to excite and sense fluorescence.

2. Description of the Prior Art

Conventionally, a biosensor of this type is an optical system comprising a waveguide to which light is coupled with a wavelength specific to a fluorescent agent that can be excited by the evanescent wave in the optical waveguide.

The immunological reaction employed in a biosensor of this type can essentially be brought about by two different methods.

In a first method, antibodies specific to an antigen to be detected are fixed on the surface of the waveguide. The sample to be analyzed, whose antigen concentration is to be ascertained, is mixed with antigens that are identical to those which are to be detected but are chemically bound to a fluorescent agent (also referred to as a "marker" or "label").

This hybrid sample is then incubated and the fluorescence excited by the evanescent wave is measured. Under these conditions, if the sample contains a high quantity of antigens (in which case it is referred to as "positive"), few antigens bound to the fluorescent agent will couple to the antibodies immobilized on the surface of the waveguide, and so weak fluorescence will be measured. However, if the sample initially contains few antigens or no antigens at all (in which case it is referred to as "negative"), those which have been added with the fluorescent agent will bind to the immobilized antibodies and strong fluorescence will be measured.

In a second method, the procedure adopted is somewhat reversed. In this case, antigens of the same type as those to be detected are bound beforehand to a protein and are immobilized on the surface of the waveguide. The sample is mixed with antibodies which are specific to this antigen but are bound to a fluorescent agent. This sample is brought into contact with the antigens immobilized beforehand on the surface of the waveguide and the fluorescence is measured after incubation.

In this case, if the sample is positive the antibodies provided with the fluorescent agent will bind to the antigens of the sample instead of binding to the antigens immobilized on the surface of the waveguide. The antigen/antibody/fluorescent-agent complexes will then remain remote from the surface of the waveguide and weak fluorescence will be measured.

However, if the sample is negative the antibodies provided with the fluorescent agent will bind to the antigens immobilized on the surface of the waveguide. The fluorescent agent can then be excited by the evanescent wave and strong fluorescence will be measured.

The measurement may be qualitative, and also quantitative if the intensity of the observed fluorescence is measured.

The waveguide may be formed by a solid substance which conducts light and on whose surface diffraction gratings may be provided for coupling into it an excitation beam originating from a light source and for extracting from it output radiation due to the fluorescence and the original radiation not converted by the fluorescence. Since the radiation due to the fluorescence has a wavelength different to that of the incident radiation, they are separated angularly by the grating and a photodetector may be placed in the beam of the fluorescence, the output signal of this photodetector being representative of the quantity of antigens present in the sample.

Measurement with a biosensor of this type suffers from interference inherent to its structure or the ambient conditions, for example the quality of coupling/decoupling of the light beams, losses of light energy in the waveguide and the effects of temperature.

In order to take an absolute measurement, it is therefore necessary to provide reference zones on the waveguide, whose fluorescence is known and which are provided in the sensor in the same way as the measurement zones, as described for example in U.S. Pat. No. 5,631,170. A reference zone is also required because the biosensor is preferably disposable and measurement conditions may therefore differ from one biosensor to another because of unavoidable manufacturing tolerances, especially pertaining to the dimensions and the surface condition of the waveguide of the biosensor.

However, these reference zones have a number of drawbacks. First, they take up space on the surface of the waveguide, thereby reducing the space available for the measurement zones.

Further, the reference zones are necessarily provided at positions other than those where the measurement zones are located and where the measurement conditions are not identical (different surface conditions, different waveguide thicknesses, etc.). The biosensor therefore has an inherent inaccuracy, in spite of the reference zones and the secondary measurement which they involve.

The aim of the invention is to provide an optical biosensor using an immunological reaction in which the measurement reference can be obtained simply and reliably without reducing the area available for the measurement, which is independent of the dimensional inaccuracy of a mass-produced biosensor.

SUMMARY OF THE INVENTION

The invention therefore consists in an optical biosensor using an immunological reaction and a fluorescent marker that can be excited by an evanescent wave, the biosensor comprising a support, an optical waveguide formed on the support, at least one diffraction grating formed in at least one surface of the waveguide for respectively coupling an excitation beam into the waveguide and decoupling a measurement beam due to fluorescence out of the waveguide, and at least one analysis element fixed in a reaction region delimited on the surface to contribute to exciting fluorescence of the marker by interaction with a sample to be analyzed, the marker having a fluorescence curve with an energy peak at a predetermined first fluorescence wavelength, in which biosensor the waveguide comprises a material whose fluorescence can be excited spontaneously in the presence of the excitation beam and the material has a spontaneous fluorescence curve having a fluorescence peak at a second wavelength different to the first wavelength.

By virtue of these features, it is possible to obtain simply and reliably, in the biosensor itself, a reference measurement for which the fluorescence is excited by the same excitation beam, the measurement being taken in the actual material of the biosensor so that it experiences the same interference as the radiation which provides the measurement data for the immunological reaction.

According to other features of the invention:

the material is silicon nitride, titanium oxide or tantalum oxide (Ta$_2$O$_5$);

the waveguide is made of a material that intrinsically exhibits the property of spontaneous fluorescence;

the waveguide is doped with a substance that exhibits this property;

the waveguide is coated with a layer made intrinsically of such a material or doped with such a material;

the biosensor comprises a diffraction grating communicating with the waveguide for coupling and decoupling the light beams;

the biosensor also comprises at least one input diffraction grating and at lest one output diffraction grating communicating with the waveguide(s);

the at least one diffraction grating is formed by lines formed in the surface by micromachining, embossing or injection molding;

the surface of the waveguide in which the at least one diffraction grating is formed has a rectangular overall shape and the lines of the diffraction grating are parallel or perpendicular to the lengthwise dimension of the surface;

the biosensor also comprises at least one coupling diffraction grating whose lines are perpendicular to the lengthwise dimension and at least one decoupling diffraction grating whose lines are parallel to this dimension;

the biosensor also comprises at least one row of decoupling diffraction gratings contiguous with a row of reaction regions which comprise as many regions as there are gratings in the row of gratings;

two rows of output diffraction gratings are arranged on respective opposite sides of a row of reaction regions;

the output diffraction gratings of the two rows are oriented to assure additive combination of the radiation that each of them decouples from the waveguide;

the reaction regions are arranged in a capillary channel for aspirating the sample;

the waveguide is further doped with at least one substance capable of exciting fluorescence having a specific third wavelength different from the first and second wavelengths; and the substance is selected from rare earths such as erbium and europium.

It is to be noted that in the present context, the expression "waveguide" encompasses both the case in which the waveguide is intrinsically made of the material exhibiting fluorescence when excited, and the case in which the waveguide is coated with such a material, which then makes part of the waveguide.

The invention also relates to a measuring system comprising a biosensor as defined above.

This system may have one or more of the following features:

it comprises a light source for illuminating the at least one diffraction grating, at least one first photodetector for detecting fluorescence decoupled from the waveguide at the first wavelength and a second photodetector for detecting fluorescence decoupled from the waveguide at the second wavelength;

the biosensor is removable.

Moreover, at least one additional photodetector may be provided for detecting fluorescence excited at the third wavelength.

BRIEF DESCRIPTION OF THE DRAWINGS

Other features and advantages of the invention will become apparent from the following description, which is given solely by way of example and refers to the appended drawings, in which:

FIG. 1 is a diagram illustrating the underlying concept of the present invention;

FIG. 2 is a highly schematic perspective view of a measuring system and a biosensor according to the invention;

FIGS. 3 and 4 are similar views showing two variants of a biosensor according to the invention;

FIG. 5 is a schematic view of a biosensor according to the invention provided with a capillary channel for guiding a sample to be analyzed;

FIGS. 6 to 9 illustrate other variants of the biosensor;

FIG. 10 is a schematic sectional view of a preferred embodiment of a biosensor according to the invention;

FIG. 11 is a simplified diagram of a complete measuring system including a biosensor according to the invention.

DETAILED DESCRIPTION OF THE PREFERRED EMBODIMENTS

The invention is based on the observation that if certain materials are used to make the waveguide in which the evanescent wave is generated it is possible to excite spontaneous fluorescence so long as sufficient optical energy density is coupled into the waveguide.

If, according to the invention, the material of the waveguide is selected in such a way that its inherent fluorescence has a curve of intensity as a function of wavelength that is offset relative to the intensity curve of the fluorescent agent used during the immunological reaction, it becomes possible to create a reference measurement in the waveguide, that is to say where the immunological reaction or reactions take place. Under these conditions, radiation coupled into the waveguide with a predetermined wavelength will be converted partly into fluorescence due to the immunological reaction and partly into radiation due to spontaneous fluorescence of the material of the waveguide. Since the fluorescence due to the immunological reaction and the radiation due to spontaneous fluorescence have different wavelengths, they can be decoupled from the waveguide at different angles and it is then easy to detect them individually using separate photodetectors.

The diagram in FIG. 1 illustrates the concept of the invention. It represents three graphs A, B and C of the relative intensity of the fluorescence as a function of the wavelength in nm.

Curves A and B are representative of two examples of specific materials that may be used for the waveguide in accordance with the invention, namely silicon nitride Si$_3$N$_4$ and titanium oxide TiO$_2$. These materials have respective fluorescence intensity peaks at about 575 nm and 610 nm. Curve C is representative of the fluorescence of an agent or marker that may be used in the immunological reaction. The substance is fluorescein whose fluorescence peak is at about 520 nm. The graph shows that the peaks of the fluorescence curves are sufficiently offset to obtain clearly distinct wavelengths for the marker and the material of the waveguide.

FIG. 2 is a schematic representation of an example of a biosensor BC according to the invention using an immunological reaction. It comprises a waveguide 1 formed by a sheet or layer of an optically transparent material which has a high refractive index and which may advantageously be deposited on a support using fabrication techniques that are well known in the field of semiconductors (see below).

By way of example, and according to the invention, the layer 1 is made at least partially of a material in which fluorescence can be excited spontaneously. Examples of materials that are particularly well-suited to this purpose are silicon nitride, titanium oxide and tantalum oxide. The waveguide consists of the entire layer or is restricted to only a part of it by photo-etching. This is true of all the embodiments and variants described below.

In order to excite spontaneous fluorescence of the waveguide of the biosensor, a material may be used for the waveguide which intrinsically exhibits this property. However, it is also possible to obtain spontaneous fluorescence by doping the waveguide with a suitable dopant or using a layer of an intrinsic or doped material deposited under or on the waveguide.

Input and output diffraction gratings 3 and 4 are formed by microlines on the surface 2 of the high-index layer 1. In this first embodiment of the invention, the microstriations are oriented transversely to the lengthwise dimension (length) of the waveguide.

The diffraction gratings may be on the lower surface or on the upper surface of the layer 1 or even on both surfaces.

There is a measurement zone 5 between the diffraction gratings 3 and 4 in which reaction regions may be located, each formed by a deposit of a component of the immunological reaction or analysis element, such as antibodies or antigens, as described above. In FIG. 2, a single reaction region is indicated by the circle 6.

The biosensor BC is integrated into a measurement system which comprises a light source 7, for example a laser, that can couple light energy into the waveguide via the input diffraction grating. This energy can excite spontaneous fluorescence in the guide. The wavelength of the source 7 preferably corresponds to the absorption maximum of the fluorescent marker (492 mm in the case of fluorescein). The fluorescence energy thus generated leaves the waveguide 1 at a specific angle $\alpha$ that depends on the wavelength of the spontaneous fluorescence of the material of which the waveguide is made. A photodetector 8 is placed on the path of this fluorescence radiation so that it can be detected as a measurement reference.

Where applicable, when the reaction region 6 has been brought into contact with a substance to be examined (for example using a pipette), the excitation radiation originating from the source 7 will also excite fluorescence at a wavelength specific to the marker used. One example of a substance that may be examined using a measurement system according to the invention is milk, when the residual concentration of antibiotics is to be determined. Since the wavelength of the marker is selected to be different to that of the spontaneous fluorescence, the radiation due to the fluorescence of the immunological reaction leaves the waveguide 1 via the output diffraction grating 4, but at an angle $\beta$ different to the aforementioned angle $\alpha$. A second photodetector 9 is placed on the path of this measurement radiation in order to detect it.

Finally, remaining light energy which is not decoupled at the angle $\alpha$ or $\beta$ leaves the waveguide at its own exit angle $\gamma$. If the support of the waveguide is transparent, the light beams can enter and leave on the support side via diffraction gratings at the interface between the waveguide and the transparent support.

In the biosensor according to the invention, the reference measurement is taken under conditions identical to those of the measurement by the immunological reaction, and so all interference effects can be taken into account without difficulty.

FIG. 3 shows a second embodiment of the invention, in which a biosensor BCA comprises a waveguide 1A in which an input diffraction grating 3A is provided for the excitation beam and a plurality of output diffraction gratings 4A-1 to 4A-6 are provided which can decouple the radiation due to the fluorescence of as many immunological reactions taking place in measurement regions 6A-1 to 6A-6 in a measurement zone 5A. The fluorescence due to the immunological reactions in these regions is here assumed to be excited by the same fluorescence marker and so the measurement radiation is decoupled from the sheet 1A at an identical angle $\alpha$ for all the measurement regions 6A-1 to 6A-6. Although this is not shown in FIG. 3, in this case the biosensor BCA is integrated into a measurement system equipped with photodetectors similar to the photodetectors 8 and 9 shown in FIG. 2. The measurement radiation originating from the decoupling diffraction gratings 4A-1 to 4A-6 is advantageously measured using a row of photodetectors comprising as many pixels as there are regions. An array of CCD cells may be used for this purpose. One or more photodetectors similar to the photodetector 8 shown in FIG. 2 should of course also be provided in order to detect decoupled radiation from at least one output diffraction grating due to spontaneous fluorescence excited in the material of the waveguide 1A. In this case it is possible to provide not only a single photodetector that detects this radiation from a single output grating but also as many photodetectors as there are output gratings in order to provide a reference measurement for all the reaction regions 6A-1 to 6A-6.

In this embodiment of the biosensor according to the invention the lines of the decoupling diffraction gratings are parallel to the lengthwise dimension of the sheet 1A.

FIG. 4 shows another embodiment of the invention, in which a waveguide 1B of the biosensor BCB comprises reaction regions 6B-1 to 6B-6 between two rows of output diffraction gratings 4B-1a to 4B-6a, on the one hand, and 4B-1b to 4B-6b, on the other hand, these rows being aligned longitudinally along the measurement zone 5B, which is illuminated by means of an input diffraction grating 3B. The output diffraction gratings are oriented in such a way that their lines are parallel to the lengthwise direction of the sheet 1B. Moreover, the rows 4B-1a to 4B-6a and 4B-1b to 4B-6b, respectively, are oriented in opposite directions so that the decoupled beams can combine additively in the photodetectors 9 (also not shown here for the sake of clarity, like the photodetector(s) 8. The photodetectors may be provided in the same way as described above with reference to FIG. 3.

FIG. 5 shows a variant biosensor BCC which is similar to the biosensor shown in FIG. 4 except that the measurement zone 5C is covered with a cover member 10 with an inverted U-shaped cross section. This cover member may, with the upper surface of the waveguide 1C of the biosensor, constitute a capillary 11 for taking up the substances to be measured.

FIG. 6 shows another biosensor variant BCD similar to the biosensor in FIG. In this case, the sheet 1D has two measurement zones 5D-1 and 5D-2 parallel to its lengthwise dimension and each comprising its own set of reaction regions. The output diffraction gratings 4D-1a to 4D-6a and 4D-1b to 4D-6b, respectively, are positioned in the same way as the gratings of the variant shown in FIG. 4, except that in each row they act on two sets of photodetectors 9 (not shown) placed side by side above the sheet 1D.

FIG. 7 shows another embodiment of the biosensor BCE according to the invention. In this case, a sheet 1E comprises an input diffraction grating 3E whose lines are oriented transversely to the lengthwise dimension of the sheet 1E. A micromachined waveguide 12 in this sheet 1E branches into three paths 12a, 12b, 12c, each feeding a respective measurement zone 5E-1, 5E-2 and 5E-3. These measurement zones are provided between diffraction gratings 13 to 16 respectively collecting the measurement radiation and reference fluorescence radiation from zone 5E-1 (gratings 13 and 14), zone 5E-2 (gratings 14 and 15) and zone 5E-3 (gratings 15 and 16). In this case, three rows of photodetectors are used for the measurement. Photodetectors for the reference measurement can be provided for each measurement zone, for example.

FIG. 8 shows another embodiment of a biosensor BCF according to the invention, comprising a support 1F on which a waveguide 17 is delimited and which comprises a single diffraction grating 18 used for coupling light energy (beam 19) into the waveguide 17 and decoupling light energy excited in it by fluorescence. The waveguide 17 comprises only one measurement zone 5F with one reaction region 6F. Thus during the analysis of a sample a measurement beam 20 and a reference beam 21 are decoupled from the waveguide via the diffraction grating 18. Photodetectors (not shown) detect the measurement and reference beams 20 and 21.

The biosensor BCG shown in FIG. 9 is a variant of the biosensor shown in the previous figure. In this case, a support 1G is likewise provided with only one diffraction grating 22, which is illuminated by an input beam 23. The grating interacts with a waveguide 24 whose width is selected so that the width of the measurement zone 5G makes it possible to provide a plurality of reaction regions 6G1, 6G2 and 6G3 side by side, this width also being that of the diffraction grating. During analysis, in addition to the reference beam (not shown here), the biosensor BCG produces three contiguous beams 25-1, 25-2 and 25-3 due to the fluorescence excited in the samples.

FIG. 10 is a cross-sectional view of a biosensor according to the invention, made by micromachining using conventional photolithography methods, for example.

A silicon substrate 26 is covered with a layer of silicon oxide 27. On this layer 27, a layer 28 of a material capable of producing radiation due to spontaneous fluorescence is selectively deposited. This layer constitutes the waveguide in the sense of the present invention. Here the layer is silicon nitride deposited by the low pressure chemical vapor deposition process. FIG. 10 shows measurement zones 29 and 30 in this layer 28 separated by a gap 31. Input and output or combined input/output diffraction gratings (not shown in FIG. 10) are machined in the layer 28 by lithographic transfer and etching with buffered hydrofluoric acid or a reactive plasma. The material used for the support of the waveguide may also be a plastics material, in which case the gratings may then also be formed in it by embossing or by injection molding. In this case, the layer forming the waveguide will be deposited on a support of the biosensor using the low temperature vapor deposition process, for example.

The reaction regions 32 are covered with a reaction substance or analysis element which comprises antibodies in this example.

A microfluidic circuit is arranged above the layer forming the waveguide. This involves a selective layer 33 of silicon oxide which is deposited at low temperature and on top of which is a cover component 34 which, with the selective layer 33, delimits a capillary channel 35 through which the sample can be aspirated to the reaction regions 31 and 32.

In all the embodiments and variants described, other advantageous features of the invention make it possible to modify the behavior of the layer of material forming the waveguide so that it exhibits specific fluorescence on excitation by the mode of the waveguide. It is possible to dope this layer of material to a larger or smaller depth in order to define this specific fluorescence, for example. Thus, according to the invention, the layer may be doped with rare earths such as erbium or europium, which have the property of giving rise to fluorescence at distinct yet similar wavelengths different but close to the wavelengths specific to the immunological reactions and the material used for the waveguide. The ratio of the intensities of fluorescence due to these dopants gives an indication of the temperature of the biosensor. The radiation, decoupled from the waveguide by a diffraction grating, can then be measured using photodetectors associated with the measurement and reference photodetectors 8 and 9 shown in FIG. 2. By processing the signals delivered by these additional photodetectors, it is possible to determine indirectly not only the power propagating through the waveguide but also the temperature of the biosensor.

The temperature signal could also be used to control the temperature of the biosensor, imposing predetermined thermal conditions on it to encourage the immunological reactions taking place in it.

FIG. 11 is a highly schematic elevation view of a measurement system in which a biosensor according to the invention may be used.

A system of this type comprises a frame (shown in outline in FIG. 11 by the square 36) on which a table 37 pivoting about a horizontal axis is mounted. This table carries a mount 38 in which disposable supports 39 can be inserted. Each support comprises a disposable biosensor 40. In the measurement position, the support 39, which is provided with V-shaped positioning grooves 41, is pressed against pins 42 secured to the frame 36 by a spring 43 which bears on the mount 38.

The light source 7 is a laser which by means of a mirror 45 illuminates locations level with the frame 38 which each contain a coupling grating 44 (FIG. 12) of the biosensor 40. The photodetector 8 receives the radiation due to spontaneous fluorescence (angle α) via a focusing lens 46.

The measurement radiation is decoupled from the waveguide of the biosensor 40 at an angle β and detected by the photodetector 9 via a focusing lens 47.

The biosensor 40 used in this measurement system is of the type described above with reference to the embodiment shown in FIG. 8. However, the biosensor 40 differs from this specific embodiment in the presence of a second coupling grating 48 via which fluorescence due to specific doping, for example with erbium or europium, as mentioned above, can be decoupled from the waveguide of the biosensor 40. The radiation is sent to a detector 49 whose output signal can be used to monitor the energy sent into the biosensor 40 by the source 7 or the temperature of the biosensor, and if appropriate control these parameters by means of a control loop (not shown).

Finally, the position of the pivoting table 37 can be finely adjusted using a micrometer screw device 50 allowing the paths of the light rays to be precisely adjusted.

There is claimed:

1. An optical biosensor for detecting an immunological reaction in a sample having associated therewith a fluorescent marker that can be excited by an evanescent wave, said biosensor comprising a support, an optical waveguide formed on said support, at least one diffraction grating formed in at least one surface of said waveguide for coupling an excitation beam into said waveguide and decoupling a measurement beam due to fluorescence by said fluorescent marker out of said waveguide at a first angle for detection by a first photodetector, and at least one analysis element for receiving said sample, said at least one analysis element being fixed in at least one reaction region delimited on one of said at least one surface in the path of said excitation beam in said waveguide to contribute to exciting fluorescence of said marker associated with said sample, wherein said marker has a fluorescence curve with an energy peak at a predetermined first wavelength, said waveguide comprises a material having a fluorescence that can be excited spontaneously in the presence of said excitation beam and said material has a spontaneous fluorescence curve having a fluorescence peak lying at a second wavelength different from said first wavelength, and wherein said second wavelength produces through said at least one diffraction grating a reference beam at an exit angle different from said first angle for detection by a second photodetector.

2. The biosensor claimed in claim 1 wherein said material is silicon nitride, titanium oxide or tantalum oxide.

3. The biosensor claimed in claim 1 wherein said waveguide is made of a material that intrinsically exhibits spontaneous fluorescence.

4. The biosensor claimed in claim 1 wherein said waveguide is doped with a substance that causes said spontaneous fluorescence when it is excited.

5. The biosensor claimed claim 1 wherein said waveguide is coated with a layer of a material that exhibits said spontaneous fluorescence when it is excited or with a layer doped with such a material.

6. The biosensor claimed in claim 1 comprising a diffraction grating communicating with said waveguide for coupling and decoupling said light beams.

7. The biosensor claimed in claim 1 comprising at least one input diffraction grating and at least one output diffraction grating communicating with said waveguide.

8. The biosensor claimed in claim 6 wherein said at least one diffraction grating is formed by lines formed in said surface by micromachining, embossing or injection molding.

9. The biosensor claimed in claim 7 wherein said at least one diffraction grating is formed by lines formed in said surface by micromachining, embossing or injection molding.

10. The biosensor claimed in claim 8 wherein the surface of said waveguide in which said at least one diffraction grating is formed has a rectangular overall shape and the lines of said diffraction grating are parallel or perpendicular to the lengthwise dimension of said surface.

11. The biosensor claimed in claim 9 wherein the surface of said waveguide in which said at least one diffraction grating is formed has a rectangular overall shape and the lines of said diffraction grating are parallel or perpendicular to the lengthwise dimension of said surface.

12. The biosensor claimed in claim 7 wherein said at least one diffraction grating is formed by lines formed in said surface by micromachining, embossing or injection molding and the surface of said waveguide in which said at least one diffraction grating is formed has a rectangular overall shape and the lines of said diffraction grating are parallel or perpendicular to the lengthwise dimension of said surface, said biosensor comprising at least one coupling diffraction grating whose lines are perpendicular to said lengthwise dimension and at least one decoupling diffraction grating whose lines are parallel to said lengthwise dimension.

13. The biosensor claimed in claim 12 comprising at least one row of decoupling diffraction gratings contiguous with at least one row of reaction regions comprising as many regions as there are gratings in said row of gratings.

14. The biosensor claimed in claim 13 wherein two rows of output diffraction gratings are arranged on respective opposite sides of a row of reaction regions.

15. The biosensor claimed in claim 14 wherein said output diffraction gratings of said two rows are oriented to assure additive combination of the radiation that each decouples from said waveguide.

16. The biosensor claimed in claim 1 wherein said reaction regions are arranged in a capillary channel for aspirating said sample.

17. The biosensor claimed in claim 1 wherein said waveguide is further doped with at least one substance capable of exciting fluorescence having at least one specific third wavelength different to said first and second wavelengths.

18. The biosensor claimed in claim 17 wherein said substance is selected from rare earths such as erbium or europium.

19. A measuring system comprising a biosensor as claimed in claim 1 which also comprises a light source for illuminating said at least one diffraction grating, at least one first photodetector for detecting fluorescence decoupled from said waveguide at said first wavelength and a second photodetector for detecting fluorescence decoupled from said waveguide at said second wavelength.

20. The measuring system claimed in claim 19 wherein said biosensor is removable.

21. A measuring system comprising a biosensor as claimed in claim 14 comprising at least one additional detector for detecting fluorescence excited at said third wavelength.

22. A measuring system comprising a biosensor as claimed in claim 15 comprising an additional detector for detecting fluorescence excited at said third wavelength.

* * * * *